United States Patent [19]

Ohtsuki et al.

[11] 4,271,353

[45] Jun. 2, 1981

[54] X-RAY SPECTROSCOPE

[75] Inventors: Nobuo Ohtsuki, Ibaraki; Eiji Yamada, Kyoto; Tadashi Utaka, Takatsuki, all of Japan

[73] Assignee: Rigaku Industrial Corporation, Takatsuki, Japan

[21] Appl. No.: 52,943

[22] Filed: Jun. 27, 1979

[30] Foreign Application Priority Data

Feb. 19, 1979 [JP] Japan .................................. 54-17272

[51] Int. Cl.³ ............................................ G01N 23/20
[52] U.S. Cl. ..................................... 250/276; 250/272
[58] Field of Search ............... 250/272, 273, 276, 274, 250/275

[56] References Cited

U.S. PATENT DOCUMENTS

| | | | |
|---|---|---|---|
| 3,160,747 | 12/1964 | De Vries | 250/276 |
| 3,160,749 | 12/1964 | Spielberg | 250/276 |

Primary Examiner—Craig E. Church

Attorney, Agent, or Firm—A. W. Breiner

[57] ABSTRACT

An X-ray Spectroscope comprising a pair of soller slits disposed such that one end of each faces an X-ray emitting portion of a sample, a pair of total reflection mirrors disposed such that one end of each face the other end of the respective soller slits and that the reflecting surfaces thereof face each other and make a predetermined angle with respect to X-rays passed through the respective soller slits and an X-ray detector disposed at a position, at which X-rays reflected by the total reflection mirrors intersect each other. If necessary, it further provides a pair of auxiliary soller slits between the X-ray detector and the total reflection mirrors and a filter capable of absorbing only characteristic X-rays from a particular substance.

Such an X-ray spectroscope has an extremely improved efficiency of detection compared to the conventional spectroscope of this kind and can also permit size reduction of the entire device.

9 Claims, 2 Drawing Figures

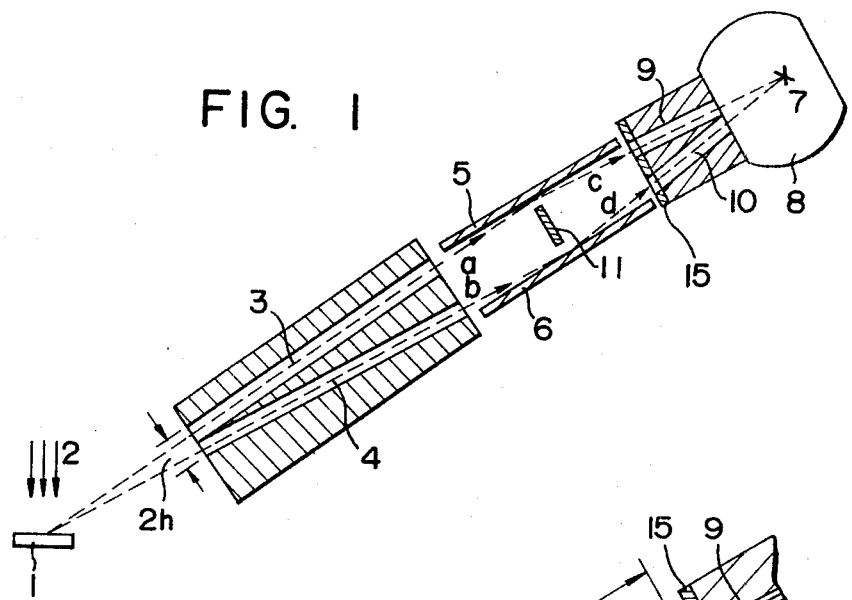
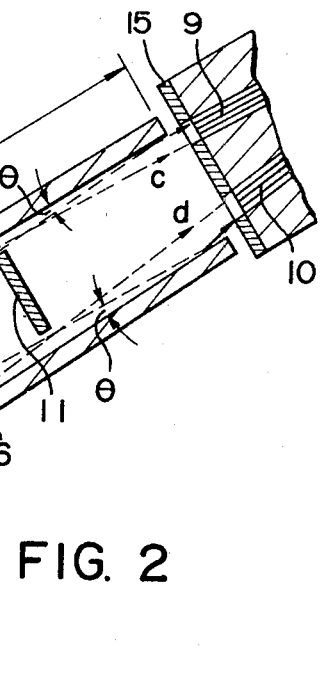
FIG. 1
FIG. 2

X-RAY SPECTROSCOPE

BACKGROUND OF THE INVENTION

1. Field of the Invention

This invention relates to X-ray spectroscopes used for spectral detection of characteristic X-rays, particularly ultra soft X-rays such as those from beryllium, boron, carbon, nitrogen and oxygen.

2. Description of the Prior Art

In the fluorescence X-ray spectrometry, detection of a substance generating ultra soft X-rays such as carbon is very difficult and requires particularly high efficiency means of the analysis because of very low efficiency of X-ray generation, usually about 0.05% at most and also high absorption of the X-rays by the substance. The spectroscopes employed hitherto have used multi-layer films of metal salt of higher fatty acid or concave diffraction gratings as mentioned in "Advances in X-Ray Analysis", Vol. 7, page 497 (1967). Their reflectivity, however, has been low, no higher than several percent, so that quantitative analysis in case with concentration of no higher than several percent such as the measurement of the carbon in iron and steel has been practically impossible.

SUMMARY OF THE INVENTION

An object of the invention is to provide an X-ray spectroscope, which uses a pair of total reflection mirrors capable of providing a reflectivity of several ten percent or above, with these mirrors disposed to face each other, so that it can provide a reflectivity of at least 20 times higher than that of the conventional spectroscope.

The invention features an X-ray spectroscope, which comprises a means for causing emission characteristic X-rays from a sample to be analyzed, a pair of soller slits disposed such that one end thereof faces the sample, a pair of total reflection mirrors disposed such that one end thereof faces the other end of the respective soller slits and that the reflecting surfaces thereof face each other and an X-ray detector disposed at a position, at which X-rays reflected by the total reflection mirrors intersect each other, with the total reflection mirrors making a predetermined angle with respect to X-rays passed through the respective soller slits.

Further objects, advantages and features of the present invention will become more fully apparent from a detailed consideration of the arrangement and construction of the constituent parts as set forth in the following specification taken together with the accompanying drawings.

BRIEF DESCRIPTION OF THE DRAWINGS

FIG. 1 is a longitudinal sectional view of an embodiment of the X-ray spectroscope according to the invention; and FIG. 2 is an enlarged-scale fragmentary sectional view showing part of the X-ray spectroscope shown in FIG. 1.

DETAILED DESCRIPTION OF THE PREFERRED EMBODIMENTS

Referring now to FIGS. 1 and 2, which show an embodiment of the X-ray spectroscope according to the invention, a sample 1 to be analyzed, for instance steel, is irradiated with primary X-rays 2 from an X-ray tube to cause generation of characteristic X-rays from beryllium, boron, carbon, nitrogen or oxygen contained in the sample for carrying out quantitative analysis of the substance through spectrometric detection of the characteristic X-rays thus generated.

A pair of soller slits 3 and 4 are disposed such that one ends thereof face an X-ray generating portion of the sample 1, and a pair of total reflection mirrors 5 and 6 are disposed such that one end of each faces the other end of the respective soller slits. The total reflection mirrors 5 and 6 have their reflection surfaces facing each other and making a predetermined angle $\theta$ with respect to X-rays a and b having passed through the respective soller slits. The angle $\theta$ is selected to such a value that total reflection takes place with the characteristic X-rays from the substance to be detected and does not with X-rays of shorter wavelengths. The characteristic X-rays c and d of the substance, generated from the sample 1 and totally reflected by the respective mirrors 5 and 6, thus intersect each other at a point 7. An X-ray detector 8 is disposed at this point of intersection, and sub-soller slits 9 and 10 are provided between the detector and the corresponding ends of the mirrors 5 and 6. A scatter stop plate 11 for blocking scattered X-rays is disposed at the center of the space defined by the mirrors 5 and 6.

The total reflection mirrors 5 and 6 are made of silicon oxide ($SiO_2$), that is, quartz glass, and the soller slits 3 and 9 are made integral with their respective mates 4 and 10.

For minimizing the absorption, the soller slits are made of $SiO_2$ blocks 12, 13 and 14, formed by finishing its single crystal and providing parallel metal foils at a small interval in the X-ray paths defined by the blocks.

With the above device, the critical angle $\theta_c$ of the total reflection mirrors is given as following formula;

$$\theta_c = \sqrt{\frac{e^2 N}{\pi m c^2} \cdot \frac{Z\rho}{M}} \cdot \lambda = 16.4 \times 10^3 \sqrt{\rho \lambda} \text{ (Radian)}.$$

(wherein
e is the electric charge of electron,
m is the mass of electron,
c is the velocity of light,
N is the Avogadro's number of the material constituting,
Z is the number of electrons per molecule,
M is the molecular weight in grams,
$\rho$ is the density in g/cm$^3$ and
$\lambda$ is the wavelength of the incident X-rays in nm.)

Thus, the critical angle is a function of the wavelength of the X-rays, and with quartz glass with density $\rho$ of 2.2 g/cm$^3$ the critical angles for K$\alpha$ radiation from beryllium, boron, carbon, nitrogen and oxygen with respective atomic numbers of 4, 5, 6, 7 and 8 are respectively 15.89, 9.42, 6.21, 4.40 and 3.29 degrees. Accordingly, by setting the angle $\theta$ to 6 degrees, for instance, it is possible to have the mirrors effect total reflection of only the characteristic X-rays from carbon and substances of smaller atomic numbers than carbon and absorb or diverge the characteristic X-rays from substances of greater atomic numbers.

For example, when the sample 1 is steel, it hardly contains boron or beryllium with the atomic numbers smaller than that of carbon, so that in this case the characteristic X-rays of only carbon are in effect spectrally separated to be incident on the detector 8. In case when the sample 1 is an alloy, the sole characteristic X-rays of carbon can be made to be incident on the detector 8 by providing a filter 15, which can absorb only the X-rays of beryllium and boron, either ahead of or behind the sub-collar slits 9 and 10. In the detector 8, the incident X-rays are converted into an electric signal and stored in a scaler circuit.

In order to make effective use of the X-rays having passed through a soller slit with an aperture height h it is necessary to use a total reflection mirror with the total length l thereof given as $h/\sin \theta$. In accordance with the invention, the two soller slits 3 and 4 with the aperture height h of, for instance, 7.3 mm and two total reflection mirrors 5 and 6 with the total length l of 75 mm are used when the incidence angle is set to 6 degrees as mentioned above, with the overall aperture height 2h of the two soller slits in this case being 15.6 mm. Thus, in this case the intensity of the X-rays having passed through the two soller slits is the same as the intensity of the X-rays having passed through a single soller slit with an aperture height of 15.6 mm. In case of making use of the X-rays having passed through such a single soller slit, however, a total reflection mirror with a total length of 150 mm is required. If such a long mirror is used, X-radiation incident on the detector is extremely reduced due to divergence of X-rays in directions perpendicular to the plane of paper of FIGS. 1 and 2. By using two soller slits and two total reflection mirrors as mentioned above it is possible to prevent attenuation of X-rays due to divergence and also construct a spectrograph of a very small size with reduction of the total length of the mirror to one half.

In addition, with the two mirrors arranged to face each other the X-rays reflected by the individual mirrors are focused, so that it is possible to obtain detection with a single X-ray detector by disposing the detector at the focal point. Further, since the two soller slits are disposed to face the X-ray generating portion of the sample 1 to be analyzed such that the X-rays having passed through the slits are incident on the respective mirrors, it is possible to obtain highly precise spectrometric analysis.

While the present invention has been described with reference to a particular embodiment thereof, it will be understood that numerous modifications may be made by those skilled in the art without actually departing from the spirit and scope of the invention as defined in the appended claims.

What we claim is:

1. An X-ray spectroscope comprising a means for causing emission of characteristic X-rays from a sample to be analyzed, a pair of soller slits disposed such that one end of each faces said sample, a pair of total reflection mirrors disposed such that one end of each faces the other end of said respective soller slits and that the reflecting surfaces thereof face each other and an X-ray detector disposed at a position at which X-rays reflected by said total reflection mirrors intersect each other, with said total reflection mirrors making a predetermined angle with respect to X-rays passed through said respective soller slits.

2. The X-ray spectroscope according to claim 1, which further provides a pair of sub-soller slits between the other end of each of said total reflection mirrors and said detector.

3. The X-ray spectroscope according to claim 1, wherein said total reflection mirrors are made of silicon oxide ($SiO_2$).

4. The X-ray spectroscope according to claim 1, wherein said pair of soller slits are integral with each other.

5. The X-ray spectroscope according to claim 2, wherein said pair of sub-soller slits are integral with each other.

6. The X-ray spectroscope according to claim 1, wherein said pair of soller slits are constituted by single crystal, mirror surface finished silicon oxide ($SiO_2$) blocks and thin metal foils arranged parallel at a small interval in their X-ray paths.

7. The X-ray spectroscope according to claim 1, wherein the critical angle $\theta_c$ of said total reflection mirrors is given as following formula:

$$\theta_c = \sqrt{\frac{e^2 N}{\pi m c^2} \cdot \frac{Z\rho}{M}} \cdot \lambda = 16.4 \times 10^{-3} \sqrt{\rho\lambda} \text{ (Radian)}.$$

(wherein
e is the electric charge of electron,
m is the mass of electron,
c is the velocity of light,
N is the Avogadro's number of the material constituting said mirrors,
Z is the number of electrons per molecule,
M is the molecular weight in grams,
$\rho$ is the density in g/cm$^3$ and
$\lambda$ is the wavelength of the incident X-rays in nm.)

8. The X-ray spectroscope according to claim 1, which further provides a filter capable of absorbing characteristic X-rays of a particular substance between said detector and said total reflection mirrors.

9. The X-ray spectroscope according to claim 1, which further provides a scatter stop means in the total reflection mirrors.

* * * * *